US00PP24898P3

(12) United States Plant Patent
Korlipara

(10) Patent No.: US PP24,898 P3
(45) Date of Patent: Sep. 16, 2014

(54) *ECHINACEA* PLANT NAMED 'FLAMINGO'

(50) Latin Name: ***Echinacea* hybrid**
Varietal Denomination: Flamingo

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 169 days.

(21) Appl. No.: 13/573,966

(22) Filed: Oct. 16, 2012

(65) Prior Publication Data

US 2014/0109275 P1 Apr. 17, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

(56) References Cited

PUBLICATIONS

Upov Pluto Plant Variety Database 20140502, retrieved on May 15, 2014, retrieved from the Internet at <http://www.upov.int/pluto/en/index.jsp> for *Echinacea* 'Supreme Flamingo', one page.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Flamingo' characterized by enlarged disc florets forming an anemone-type inflorescence, light coral pink ray florets and darker coral pink disc florets, inflorescences with dark centers when the disc florets are not fully opened, a medium small size, narrow, upright habit with excellent basal stem count, and excellent vigor.

1 Drawing Sheet

Botanical denomination: *Echinacea* hybrid.
Variety designation: 'Flamingo'.

BACKGROUND OF THE INVENTION

The present invention relates to a new and distinct cultivar of *Echinacea* and given the cultivar name 'Flamingo'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Secret Passion' (U.S. Plant patent application Ser. No. 12/931,231, now U.S. Plant Pat. No. 23,018), the new cultivar is much smaller plant with a narrower and more compact habit, and the inflorescences are smaller and have dark centers before the disc florets mature.

Compared to *Echinacea* 'Secret Desire' (U.S. Plant patent application Ser. No. 13/066,145, now U.S. Plant Pat. No. 23,085), the new cultivar is much shorter and the inflorescences are pinker colored.

This new *Echinacea* cultivar is distinguished by:

1. enlarged disc florets forming an anemone-type inflorescence,
2. light coral pink ray florets and darker coral pink disc florets,
3. inflorescences with dark centers when the disc florets are not fully opened,
4. a medium short size and narrow, upright habit with excellent basal stem count, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Flamingo' growing in the garden in full sun in early July in Canby, Oreg.

DETAILED PLANT DESCRIPTION

The following is a detailed description of the new *Echinacea* cultivar based on observations of two-year-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, $5^{th}$ edition.

Plant:

*Type*.—Herbaceous perennial.

*Hardiness*.—USDA Zones 4 to 9.

*Size*.—Grows to about 38 cm wide and 51 cm tall to top of inflorescences.

*Form*.—Basal clump, with about 28 stems from the base.

*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 3 inflorescences per stem.

*Size*.—To 45 cm tall to a terminal inflorescence and 1 cm wide at base.

*Internode length*.—1 cm to 5 cm.

*Surface texture*.—Strigose.

*Color*.—Yellow Green 146C tinted Greyed Purple 183A.

Leaf (basal):

*Type*.—Simple.

*Shape*.—Lanceolate.

*Arrangement*.—Basal.

*Blade size*.—Grows to 8.5 cm long and 3.1 cm wide.

*Margins*.—Entire.

*Apex*.—Acute.

*Base*.—Attenuate.

*Surface texture*.—Strigose on both sides.

*Venation*.—Pinnate, Green N137A on top and Yellow Green 149A on bottom side.

*Color*.—Topside Green N137A, bottom side closest to Yellow Green 147B.

*Petiole description*.—Clasping, grows to 8 cm long, sparsely strigose, Greyed Purple 187A on top side and Yellow Green 146B on bottom side.

Leaf (stem):

*Type*.—Simple.

*Shape*.—Lanceolate.

*Arrangement*.—Alternate.

*Blade size*.—Grows to 15.5 cm long and 5.5 cm wide.

*Margins*.—Serrate.

*Apex*.—Acuminate.

*Base*.—Attenuate.

*Surface texture*.—Strigose on both sides.

*Venation*.—Pinnate, with 3 main veins from the base, Green N137A on top and Yellow Green 149A on bottom side.

*Color*.—Topside Green N137A, bottom side closest to Yellow Green 147B.

*Petiole description*.—On all but upper leaves, clasping, grows to 8 cm long and 5 mm wide above the clasp, sparsely strigose, Yellow Green 146B on sides and Yellow Green 149A in middle.

Inflorescence:

*Type*.—Composite on terminal stalked heads.

*Number of flowering stems per plant*.—About 28.

*Flowering stem*.—Grows to 45 cm tall from the base of the plant to the terminal inflorescence and can grow to 11 cm to 13 cm long from the top stem leaf to the base of an inflorescence; branched with 1 to 3 inflorescences per stem; diameter growing to 12 mm wide near the inflorescence; strigose; Yellow Green 146C tinted Greyed Purple 183A.

*Size*.—Grows to 9 cm wide and 5.5 cm deep as disc enlarges.

*Form*.—Ray florets held slightly reflexed, mature disc is conic.

*Immature inflorescence*.—Grows to 2.5 cm wide and 1.9 cm deep, ray florets held at a 70 degree angle from the vertical and rolled up so only the back color shows, Red Purple 59A, disc color Greyed Purple 187A.

*Ray florets*.—Without pistil or stamen, about 16 in number, grow to 42 mm long and 11 mm wide, oblanceolate with the tip two to three-toothed (each acute, middle tooth sometimes vertical), entire margins, base attenuate, glabrous on both sides; topside young Red Purple 58A on base blending to Orange Red 31A at the apex, when mature Red Purple 58A on base blending to Orange Red 31A at the apex, bottom side Red Purple 60C.

*Disc*.—Flat becoming conic, growing to 27 mm deep and 55 mm wide with maturity, Greyed Purple 187A when disc florets are closed to Red 39B when disc florets are open.

*Disc florets*.—About 360 in number, each with 1 pistil and 0 stamen, grow to 27 mm long and 7 mm wide, each with one persistent, very stiff linear bract (12 mm long with the Greyed Purple 187A on tip then Orange 24B in middle then Yellow Green 145D); corollas 17 mm long and 7 mm wide, tubular at base (2.5 mm to 7 mm long and 1.5 mm wide, 166A) then a fan-like corolla, margin entire, tips acute, base attenuate, glabrous on both sides, 14 mm to 17 mm long and 5 mm to 7 mm wide, with 2 to 4 lobes (usually 3), lobes 2 mm to 5 mm long and 1 mm to 2 mm wide, topside Red 48A, bottom side closest to Greyed Purple 185D; pistil 10 mm long, ovary 4 mm long, White 155A, style 5 mm long Red Purple 60A, 2-branched stigma spreading, Greyed Purple 187A; stamen 4 mm long, filaments 4 mm long, threadlike, Yellow Green 145D, anthers none, pollen none.

*Phyllaries*.—In 4 leafy series, area grows to 30 mm wide and 7 mm deep, lobes lanceolate in shape, reflexed, grow to 12 mm long and 4 mm wide, Green N137A, margins strigose, tip acute, strigose on both sides.

*Receptacle*.—Grows to 13 mm wide and 11 mm deep, White NN155B.

*Bloom period*.—July through October in Canby, Oreg.

*Fragrance*.—Light, floral.

*Lastingness*.—Each inflorescence lasts about two weeks in Canby, Oreg.

*Seeds*.—None.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

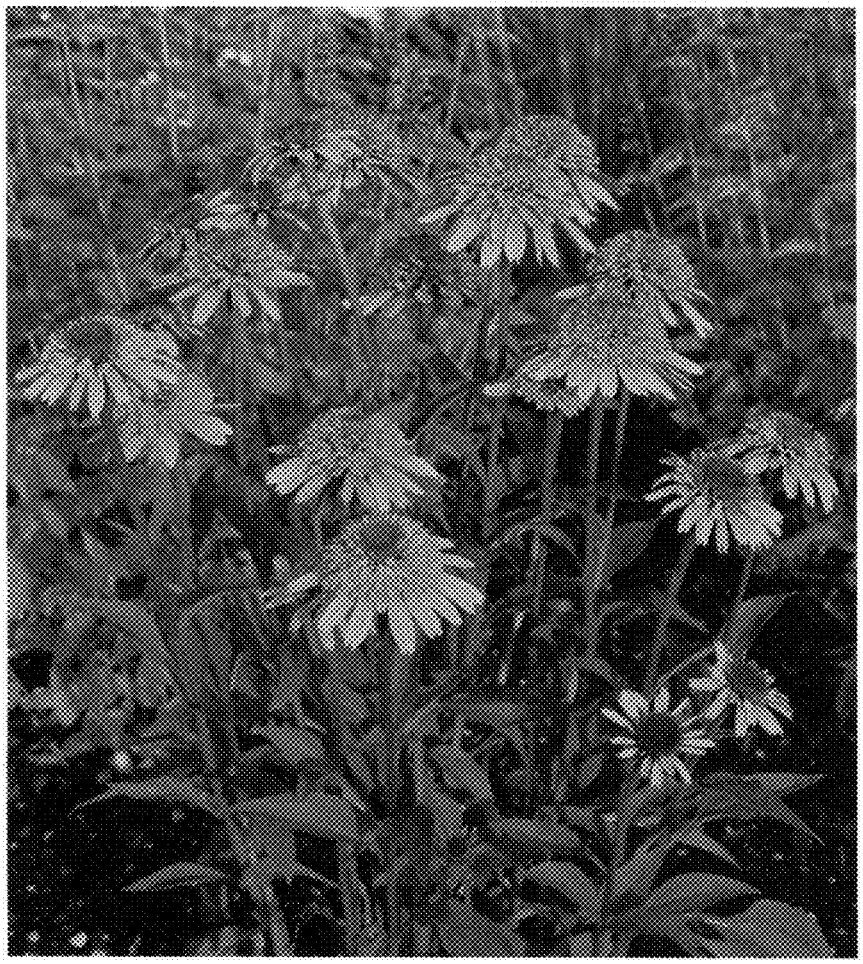

* * * * *